United States Patent
Augoyard et al.

(10) Patent No.: US 9,283,007 B2
(45) Date of Patent: Mar. 15, 2016

(54) DEVICE FOR OSTEOSYNTHESES OR ARTHRODESES OF TWO- BONE PARTS, IN PARTICULAR OF THE HAND AND / OR FOOT

(71) Applicant: MEMOMETAL TECHNOLOGIES, Bruz (FR)

(72) Inventors: Marc Augoyard, Tassin La Demi Lune (FR); Jacques Peyrot, Tassin La Demi Lune (FR); Tristan Meusnier, Saint-Etienne (FR); Bernard Prandi, Rennes (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 320 days.

(21) Appl. No.: 13/897,775

(22) Filed: May 20, 2013

(65) Prior Publication Data

US 2013/0253515 A1   Sep. 26, 2013

Related U.S. Application Data

(63) Continuation of application No. 11/911,405, filed as application No. PCT/FR2006/050435 on Oct. 19, 2006, now Pat. No. 8,475,456.

(30) Foreign Application Priority Data

Apr. 14, 2005 (FR) ...................................... 05 50957

(51) Int. Cl.
*A61B 17/72* (2006.01)
*A61B 17/68* (2006.01)
(Continued)

(52) U.S. Cl.
CPC ................ *A61B 17/72* (2013.01); *A61B 17/68* (2013.01); *A61B 17/7208* (2013.01);
(Continued)

(58) Field of Classification Search
CPC ................ A61F 2002/4246; A61F 2002/4248; A61B 17/844; A61B 17/7208
See application file for complete search history.

(56) References Cited

U.S. PATENT DOCUMENTS

| | | |
|---|---|---|
| 3,462,765 A | 8/1969 | Swanson |
| 3,466,669 A | 9/1969 | Flatt |

(Continued)

FOREIGN PATENT DOCUMENTS

| | | |
|---|---|---|
| CA | 2836654 A1 | 6/2014 |
| CA | 2837497 A1 | 6/2014 |

(Continued)

OTHER PUBLICATIONS

International Search Report for PCT/FR2008/050453 dated Nov. 4, 2008.

(Continued)

*Primary Examiner* — Christian Sevilla
(74) *Attorney, Agent, or Firm* — Lerner, David, Littenberg, Krumholz & Mentlik, LLP

(57) ABSTRACT

In one embodiment the present invention is an implant suitable for implantation in bone, comprising a median zone extending along a longitudinal axis between a first end and a second end, the first end having a face extending generally perpendicular to the axis to form an abutment having a width; and a first fixation zone extending from the first end and the abutment, the first fixation zone including a pair of tabs formed of shape-memory material extending from a base portion of the tabs adjacent the abutment such that the abutment extends further from the axis in a radial direction than the base portion of the tabs, wherein the pair of tabs are separable from one another by shape-memory action at body temperature.

20 Claims, 2 Drawing Sheets

(51) Int. Cl.
*A61B 17/84* (2006.01)
*A61B 17/00* (2006.01)
*A61F 2/30* (2006.01)
*A61F 2/42* (2006.01)

(52) U.S. Cl.
CPC ........ *A61B 17/7225* (2013.01); *A61B 17/7266* (2013.01); *A61B 17/7291* (2013.01); *A61B 17/844* (2013.01); *A61B 2017/00867* (2013.01); *A61F 2002/30093* (2013.01); *A61F 2002/30622* (2013.01); *A61F 2002/4243* (2013.01); *A61F 2210/0019* (2013.01)

(56) References Cited

U.S. PATENT DOCUMENTS

| | | |
|---|---|---|
| 3,593,342 A | 7/1971 | Niebauer et al. |
| 3,681,786 A | 8/1972 | Lynch |
| 3,739,403 A | 6/1973 | Nicolle |
| 3,805,302 A | 4/1974 | Mathys |
| 3,824,631 A | 7/1974 | Burstein et al. |
| 3,875,594 A | 4/1975 | Swanson |
| D243,716 S | 3/1977 | Treace et al. |
| 4,158,893 A | 6/1979 | Swanson |
| 4,204,284 A | 5/1980 | Koeneman |
| 4,276,660 A | 7/1981 | Laure |
| 4,364,382 A | 12/1982 | Mennen |
| 4,367,562 A | 1/1983 | Gauthier et al. |
| D277,509 S | 2/1985 | Lawrence et al. |
| D277,784 S | 2/1985 | Sgarlato et al. |
| 4,522,200 A | 6/1985 | Stednitz |
| D284,099 S | 6/1986 | Laporta et al. |
| 4,634,382 A | 1/1987 | Kusano et al. |
| D291,731 S | 9/1987 | Aikins |
| 4,759,768 A | 7/1988 | Hermann et al. |
| 4,871,367 A | 10/1989 | Christensen et al. |
| 4,955,916 A | 9/1990 | Carignan et al. |
| 4,969,909 A | 11/1990 | Barouk |
| 5,011,497 A | 4/1991 | Persson et al. |
| 5,047,059 A | 9/1991 | Saffar |
| 5,062,851 A | 11/1991 | Branemark |
| 5,092,896 A | 3/1992 | Meuli et al. |
| 5,108,443 A | 4/1992 | Branemark |
| 5,133,761 A | 7/1992 | Krouskop |
| 5,179,915 A | 1/1993 | Cohen et al. |
| 5,190,546 A | 3/1993 | Jervis |
| 5,207,712 A | 5/1993 | Cohen |
| 5,326,364 A | 7/1994 | Clift, Jr. et al. |
| 5,405,400 A | 4/1995 | Linscheid et al. |
| 5,405,401 A | 4/1995 | Lippincott, III et al. |
| 5,425,776 A | 6/1995 | Cohen |
| 5,425,777 A | 6/1995 | Sarkisian et al. |
| 5,474,557 A * | 12/1995 | Mai ................................ 606/78 |
| 5,480,447 A | 1/1996 | Skiba |
| 5,484,443 A | 1/1996 | Pascarella et al. |
| 5,507,822 A | 4/1996 | Bouchon et al. |
| 5,522,903 A | 6/1996 | Sokolow et al. |
| 5,554,157 A | 9/1996 | Errico et al. |
| 5,634,925 A | 6/1997 | Urbanski |
| 5,674,297 A | 10/1997 | Lane et al. |
| 5,702,472 A | 12/1997 | Huebner |
| 5,725,585 A | 3/1998 | Zobel |
| 5,782,927 A | 7/1998 | Klawitter et al. |
| 5,824,095 A | 10/1998 | Di Maio, Jr. et al. |
| 5,876,434 A | 3/1999 | Flomenblit et al. |
| 5,882,444 A | 3/1999 | Flomenblit et al. |
| 5,919,193 A | 7/1999 | Slavitt |
| 5,951,288 A | 9/1999 | Sawa |
| 5,958,159 A | 9/1999 | Prandi |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,146,387 A | 11/2000 | Trott et al. |
| 6,197,037 B1 | 3/2001 | Hair |
| 6,200,330 B1 | 3/2001 | Benderev et al. |
| 6,248,109 B1 | 6/2001 | Stoffella |
| 6,319,284 B1 | 11/2001 | Rushdy et al. |
| 6,352,560 B1 | 3/2002 | Poeschmann et al. |
| 6,383,223 B1 | 5/2002 | Baehler et al. |
| 6,386,877 B1 | 5/2002 | Sutter |
| 6,423,097 B2 | 7/2002 | Rauscher |
| 6,428,634 B1 | 8/2002 | Besselink et al. |
| 6,454,808 B1 | 9/2002 | Masada |
| 6,475,242 B1 | 11/2002 | Bramlet |
| 6,689,169 B2 | 2/2004 | Harris |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,811,568 B2 | 11/2004 | Minamikawa |
| 6,869,449 B2 | 3/2005 | Ball et al. |
| 7,037,342 B2 | 5/2006 | Nilsson et al. |
| 7,041,106 B1 | 5/2006 | Carver et al. |
| 7,182,787 B2 | 2/2007 | Hassler et al. |
| 7,240,677 B2 | 7/2007 | Fox |
| 7,291,175 B1 | 11/2007 | Gordon |
| 7,588,603 B2 | 9/2009 | Leonard |
| 7,780,737 B2 | 8/2010 | Bonnard et al. |
| 7,837,738 B2 | 11/2010 | Reigstad et al. |
| 7,842,091 B2 | 11/2010 | Johnstone et al. |
| 7,955,388 B2 | 6/2011 | Jensen et al. |
| 8,100,983 B2 | 1/2012 | Schulte |
| 8,262,712 B2 | 9/2012 | Coilard-Lavirotte et al. |
| 8,394,097 B2 | 3/2013 | Peyrot et al. |
| 8,414,583 B2 | 4/2013 | Prandi et al. |
| 8,475,456 B2 | 7/2013 | Augoyard et al. |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 2001/0025199 A1 | 9/2001 | Rauscher |
| 2002/0019636 A1 | 2/2002 | Ogilvie et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0082705 A1 | 6/2002 | Bouman et al. |
| 2003/0040805 A1 | 2/2003 | Minamikawa |
| 2003/0069645 A1 | 4/2003 | Ball et al. |
| 2003/0130660 A1 | 7/2003 | Levy et al. |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0220678 A1 | 11/2004 | Chow et al. |
| 2005/0119757 A1 | 6/2005 | Hassler et al. |
| 2005/0251265 A1 | 11/2005 | Calandruccio et al. |
| 2005/0283159 A1 * | 12/2005 | Amara ............................ 606/75 |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0185584 A1 | 8/2007 | Kaufmann et al. |
| 2007/0213831 A1 | 9/2007 | de Cubber |
| 2007/0239158 A1 | 10/2007 | Trieu et al. |
| 2008/0039949 A1 | 2/2008 | Meesenburg et al. |
| 2008/0132894 A1 | 6/2008 | Coilard-Lavirotte et al. |
| 2008/0154385 A1 | 6/2008 | Trail et al. |
| 2008/0177262 A1 | 7/2008 | Augoyard et al. |
| 2008/0195219 A1 | 8/2008 | Wiley et al. |
| 2008/0221697 A1 | 9/2008 | Graser |
| 2008/0221698 A1 | 9/2008 | Berger |
| 2008/0269908 A1 | 10/2008 | Warburton |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1 | 5/2010 | Peyrot |
| 2010/0131072 A1 | 5/2010 | Schulte |
| 2010/0161068 A1 | 6/2010 | Lindner et al. |

(56) References Cited

U.S. PATENT DOCUMENTS

| | | |
|---|---|---|
| 2010/0185295 A1 | 7/2010 | Emmanuel |
| 2010/0249942 A1 | 9/2010 | Goswami et al. |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0301652 A1 | 12/2011 | Reed et al. |
| 2012/0065692 A1 | 3/2012 | Champagne et al. |
| 2013/0053975 A1 | 2/2013 | Reed et al. |
| 2013/0060295 A1 | 3/2013 | Reed et al. |
| 2013/0066435 A1 | 3/2013 | Averous et al. |
| 2013/0131822 A1 | 5/2013 | Lewis et al. |
| 2013/0150965 A1 | 6/2013 | Taylor et al. |
| 2014/0058462 A1 | 2/2014 | Reed et al. |
| 2014/0142715 A1 | 5/2014 | McCormick |
| 2014/0180428 A1 | 6/2014 | McCormick |
| 2014/0188239 A1 | 7/2014 | Cummings |

FOREIGN PATENT DOCUMENTS

| | | |
|---|---|---|
| EP | 0420794 A1 | 4/1991 |
| EP | 1300122 A2 | 4/2003 |
| EP | 1923012 A1 | 5/2008 |
| FR | 2725126 A1 | 4/1996 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A | 5/2004 |
| FR | 2846545 A1 | 5/2004 |
| FR | 2884406 | 10/2006 |
| GB | 2119655 A | 11/1983 |
| GB | 2430625 A | 4/2007 |
| GB | 2430625 B | 4/2007 |
| JP | 60145133 A | 7/1985 |
| JP | 03-001854 A | 8/1991 |
| JP | 7303662 | 11/1995 |
| JP | 2004535249 A | 11/2004 |
| JP | 2007530194 A | 11/2007 |
| JP | 2008188411 A | 8/2008 |
| JP | 2008537696 A | 9/2008 |
| WO | 9733537 A1 | 9/1997 |
| WO | 2005063149 A1 | 7/2005 |
| WO | 2005104961 A1 | 11/2005 |
| WO | 2006109004 A1 | 10/2006 |
| WO | 2008057404 A2 | 5/2008 |
| WO | 2009103085 A1 | 8/2009 |
| WO | 2011130229 A1 | 10/2011 |

OTHER PUBLICATIONS

International Search Report, PCT/FR2006/050345, dated Aug. 30, 2006.

* cited by examiner

DEVICE FOR OSTEOSYNTHESES OR ARTHRODESES OF TWO- BONE PARTS, IN PARTICULAR OF THE HAND AND / OR FOOT

CROSS-REFERENCE TO RELATED APPLICATIONS

The present application is a continuation of U.S. patent application Ser. No. 11/911,405, filed Mar. 17, 2008, which is a national phase entry under 35 U.S.C. §371 of International Application No. PCT/FR2006/050345, filed Apr. 12, 2006, which claims priority of PCT patent application PCT/FR2006/050345 filed Apr. 12, 2006, all of which are herewith incorporated by reference.

FIELD OF THE INVENTION

The invention relates to the technical field of orthopaedic implants, particularly for arthrodeses and osteosyntheses.

It may be recalled that the object of an arthrodesis is to obtain very good stability both primary and secondary, and to place, or to maintain, in compression, two bone parts or bone fragments that should be consolidated. Stability is a critical factor for obtaining consolidation, while minimizing the attendant problems such as pain, swelling, etc. The compressive action serves to consolidate the osteotomy more rapidly in the position selected by the surgeon during the operation.

Various technical solutions have been proposed for carrying out an arthrodesis, particularly in the foot, the hand, the wrist, etc. Mention can be made, for example, of basic staples without shape memory which do not produce a compression, as opposed to memory staples which serve to place the two bone parts to be consolidated in compression, which corresponds to the objective.

However, to obtain satisfactory stability, it is necessary to place two, or even three staples, in different planes. This increases the dimensions considerably, thereby limiting applications (metacarpo-phalangeal joint, for example).

Extramedullary plates and screws have also been proposed, requiring an alternatively large dimension. In this respect, their miniaturization is difficult to conceive, because this could raise problems of strength and stiffness. Some types of screws can be used in intramedullary osteosynthesis, but they raise positioning difficulties (passage through the pad in particular).

Use can also be made of pins which have a smaller size. However, the stability obtained is unsatisfactory and it is necessary to withdraw them.

Intramedullary nails are also known, but they require supplementary stapling in order to prevent the bone parts to be joined from rotating relative to each other.

OBJECT OF THE INVENTION

It is the object of the invention to remedy these drawbacks simply, safely, effectively and efficiently.

The problem that the invention proposes to solve is to permit the fixation of two bone parts to one another, rigidly with dynamic and retentive compression, in order to obtain a reliable and rapid osteosynthesis.

SUMMARY OF THE INVENTION

To solve such a problem, an intramedullary arthrodesis element has been designed and developed which consists of a body with an elongated shape having, in succession, from one of its ends, a fixation zone cooperating with one of the bone parts to be immobilized, a median zone suitable for withstanding shear and bending stresses, and a fixation zone in the other bone part to be immobilized, each of the fixation zones being profiled and made from a material suitable for enabling introduction into the bone parts without a finger- or toe-tip approach, followed by a fixation in the bone parts, while avoiding any rotational movement, withstanding the tensile stresses, and maintaining a compressive force.

The invention has a particularly advantageous application, which can however not be considered as limiting, for the preparation of arthrodesis in the proximal and median phalanges, for proximal interphalangeal joints and distal interphalangeal joints, in the hand or foot.

To solve the problem of taking account of the anatomy, and particularly of the internal shrinkage of the bone, the median zone is linked to at least one of the fixation zones by a connecting zone.

To solve the problem of permitting implantation of the element followed by compression of the bone fragments, the fixation zones are made from a shape-memory material to be deformed by thermal and/or mechanical action.

To produce the fixation zones, which may be identical or not, various technical solutions are feasible, according in particular to the type of arthrodesis performed and the joints to be treated.

For example:

one of the fixation zones has two tabs or wings separable under the action of the shape memory;

one of the fixation zones has a tab or rod which can be curved under the action of the shape memory;

one of the fixation zones has, in its thickness, a slot for permitting deformation by elasticity, or memory, under the action of the shape memory.

In one embodiment, the overall body has a flat cross-section.

BRIEF DESCRIPTION OF THE DRAWING

The invention is described below in greater detail in conjunction with the figures of the drawings appended hereto in which.

SPECIFIC DESCRIPTION

Figure 1:
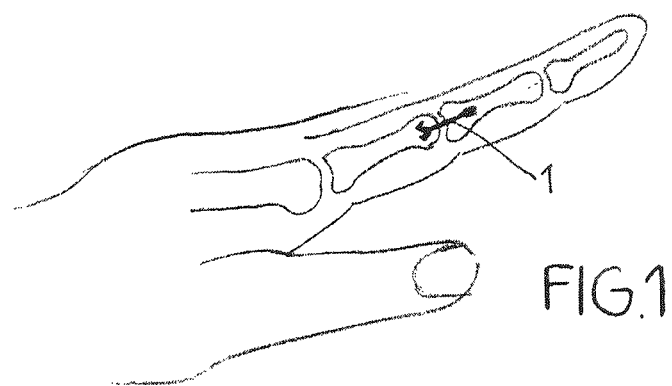
FIG. 1 is a schematic plan view showing the placement of the intramedullary arthrodesis element of the invention between a proximal phalange and a median phalange to consolidate the proximal interphalangeal joint.

The arthrodesis element of the invention consists of an elongated body 1. Each of the ends of the body 1 is conformed to produce a fixation zone 1a linked to a fixation zone 1b.

Between the two fixation zones 1a and 1b, at least one median zone 1c is formed capable of withstanding shear and bending stresses. In general, the shear and bending stresses are applied to the bone site to be consolidated. The shape of this median zone 1c is adapted to the internal shape of the bone. Its length is determined in order to allow a slight offset in the centering.

For information, and in a non-limiting manner, this median zone may have a rectangular cross-section measuring about 2 to 3 mm*1 to 1.5 mm and a length of about 3 to 5 mm for the foot and the hand.

The fixation zones 1a and 1b are conformed to prevent any rotational movement, resist tension, and maintain manual compression applied at the time of the implant by the surgeon in order to reduce the site. To obtain this result, the fixation zones 1a and 1b are made from a shape-memory material to be deformed by thermal action (tepid memory) or mechanical action (superelasticity) (see U.S. Pat. No. 5,958,159). The goal, in the fixation zones, considering their profile on the one hand and the type of material on the other, is to permit an introduction into the bone parts, particularly dorsally without a finger- or toe-tip approach, on the one hand, and to produce a fixation in the bone portion in order to obtain or to maintain the desired compressive force, on the other. The fixation zones 1a and 1b are identical or not, according to the type of bone and its morphology.

Depending on the type of arthrodesis performed, that is, the type of interphalangeal joint to be consolidated for example, the fixation zones 1a and 1b may have different embodiments.

For example, one of the fixation zones 1a has two tabs or wings that are separable under a thermal action for example. Otherwise, these fixation zones 1a may have a single tab or rod which can be curved under the action of a memory of the component material. Otherwise, the fixation zone 1b has, in its thickness, a slot to permit deformation by elasticity, under thermal action for example, and to maintain the position by pressing on the length of the bone.

According to another feature of the invention, to take account of the anatomy of the various phalanges for example, that is the internal shrinkage of the bone (hourglass shape), the median zone 1c is linked to at least one of the fixation zones 1b by a thinner connecting zone 1d.

Reference can be made to the figures of the drawings which show an embodiment of an intramedullar arthrodesis element.

In this embodiment, the body 1 has, at one of its ends, a fixation zone 1a in the form of two tabs or wings 1a1 1a2. This fixation zone 1a is prolonged by a median zone 1c of generally substantially triangular shape in a plan view. The median zone 1c is connected to the other end fixation zone 1b by a connecting zone 1d having a generally rectangular shape in a plan view. The fixation zone 1b has, in its thickness, a slot of generally oblong shape 1b1.

Figures 2, 3:
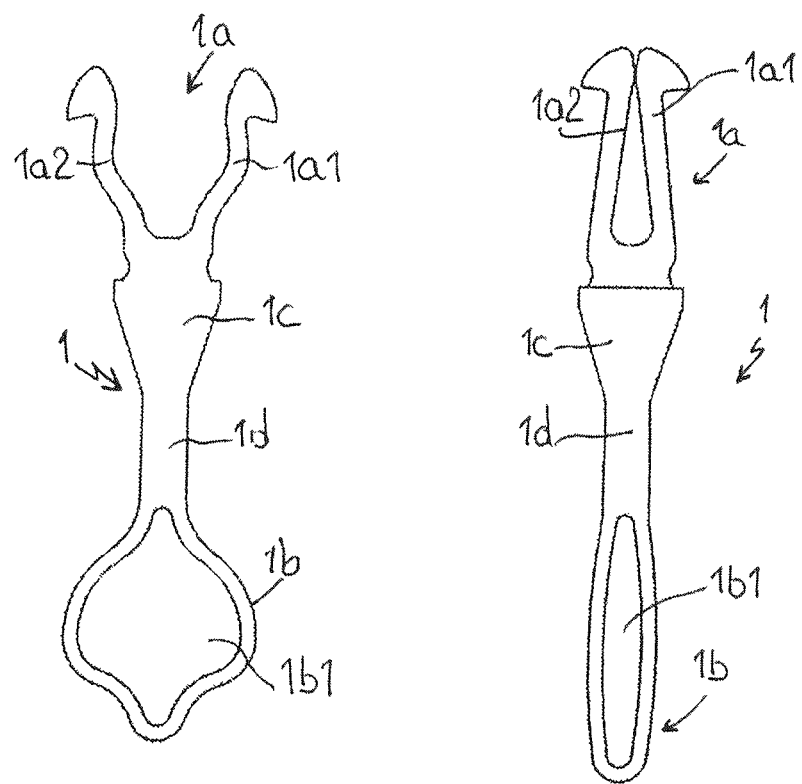
FIG. 2 is a plan view of an embodiment of the arthrodesis element at the time of its introduction.
FIG. 3 is a view corresponding to FIG. 2 showing the arthrodesis element after its implant to produce the compression.
Figure 4:
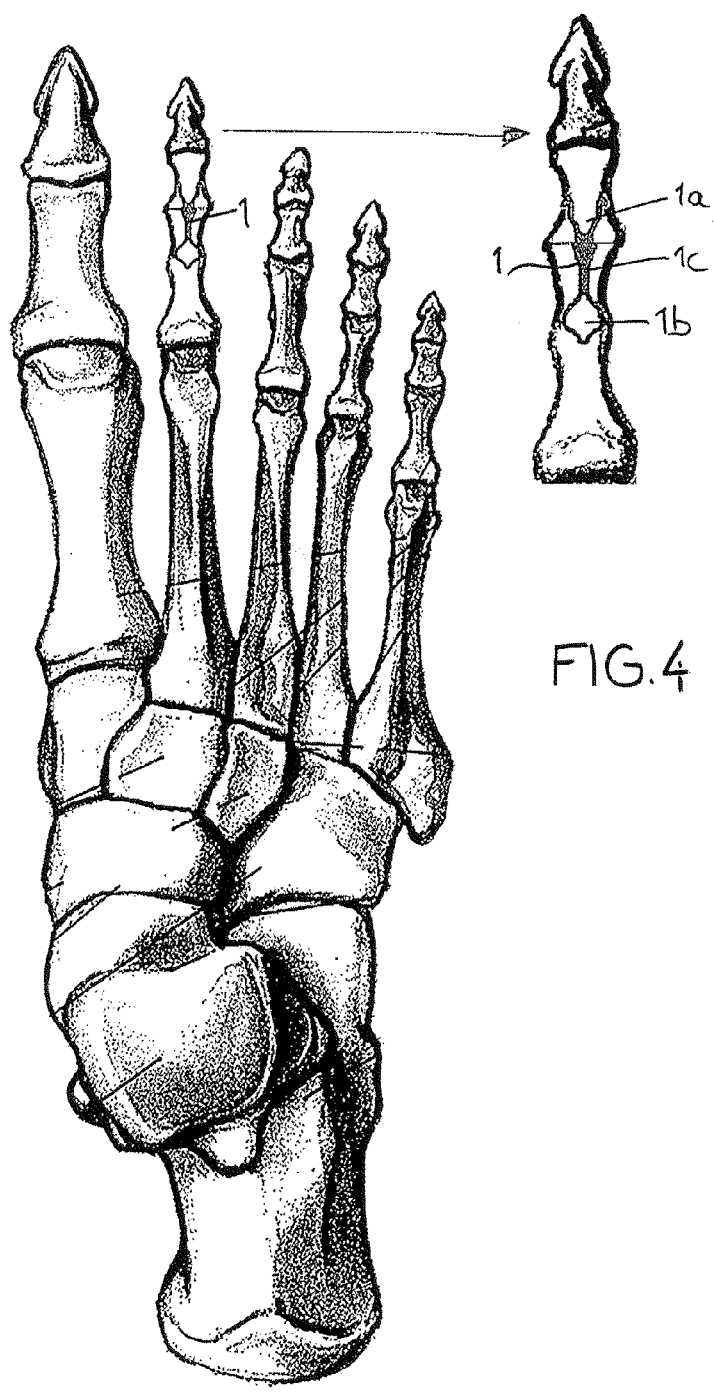
FIG. 4 shows the placement of the element of the invention in a toe.

Reference can be made to FIG. 2 which shows the element at the time of its introduction, that is before separation of the tabs 1a1 and 1a2, and the opening of the slot 1b1. For example, this configuration is obtained when the overall element is subject to a temperature much lower than that of the human body for example. Conversely, after implantation (FIG. 3), under the effect of body heat, the tabs 1a1 and 1a2 separate, in the same way as the slot 1b1, concomitantly causing a deformation of the fixation zone 1b.

It should be noted that the profile of the median zone 1c prevents penetration when the site is reclosed.

In an alternative embodiment, the connecting zone 1d can be split to benefit from a swelling effect by shape memory and strengthening of the anchoring in the diaphyseal zone.

It should be recalled that the inventive element is ideal for the treatment of the hammer- or claw-toe syndrome, by performing an arthrodesis in the phalanges P1 and P2 on the radii 2 to 5, while observing that such applications must not be considered as limiting, by means of essentially dimensional adjustments (finger reimplants, arthrodesis of the distal interphalangeal joint and of the proximal interphalangeal joint of the hand, and the arthrodesis of the big toe).

Obviously, the entire arthrodesis element of the invention may have constructive features suitable for improving the fixation and compression in particular.

For example:

notches on the tabs on one of the sides for better fixation in the ethmoid bone;

wavy tabs implanted (straight before implant) to permit shortening and hence an additional compression of the arthrodesis site compared with a simple fixation;

a tapered central zone to avoid undesirable penetration of the implant at the time when the site is to be closed.

For information, the memory used is preferably a tepid memory, so that heating is unnecessary because of the lack of access. The opening begins at above 15 to 20° C. and stops at about 30 to 35° C.

The operating technique remains conventional.

The invention claimed is:

1. An implant suitable for implantation in bone, comprising:
    a median zone extending along a longitudinal axis between a first end and a second end, the first end having a face extending generally perpendicular to the axis to form an abutment having a width; and
    a first fixation zone extending from the first end and the abutment, the first fixation zone including a pair of tabs formed of shape-memory material extending from a base portion of the tabs adjacent the abutment such that the abutment extends further from the axis in a radial direction than the base portion of the tabs, wherein the pair of tabs are separable from one another by shape-memory action at body temperature.

2. The implant of claim 1, wherein the pair of tabs has a tip portion at a location away from the abutment, wherein the tip portion extends further from the axis in the radial direction than the abutment once the pair of tabs undergo shape-memory action at body temperature.

3. The implant of claim 1, further comprising a connecting zone extending from the second end of the median zone.

4. The implant of claim 3, further comprising a second fixation zone extending from the connecting zone.

5. The implant of claim 1, further comprising a second fixation zone extending along the axis away from the second end of the median zone, the second fixation zone includes a length and a slot along a portion of the length, the second fixation zone formed of shape-memory material such that the second fixation zone is capable of changing shape by shape-memory action at body temperature.

6. The implant of claim 5, wherein the slot of the second fixation zone has a narrow oblong shape prior to changing shape by shape-memory action at body temperature and a wide oblong shape, which is wider than the narrow oblong shape, after changing shape by shape-memory action at body temperature.

7. An implant suitable for implantation in bone, comprising:
    a median zone extending along a longitudinal axis between a first end having a first width and a second end;
    a first fixation zone extending from the first end, the first fixation zone including a pair of tabs formed of shape-memory material extending from a base portion of the tabs adjacent the first end, wherein the pair of tabs are separable from one another by shape-memory action at body temperature; and
    a connecting zone of a predetermined length extending from the second end of the median zone, the connecting zone having a second width at a first end, adjacent the second end of the median zone, the second width being less than the first width of the median zone.

8. The implant of claim 7, wherein the connecting zone is of generally rectangular shape and has a pair of side faces extending substantially parallel to the axis.

9. The implant of claim 8, wherein the median zone further includes, at the first end, a face extending generally perpendicular to the axis to form an abutment having a width.

10. The implant of claim 9, wherein the abutment has the first width and the second width of the connecting zone is less than the first width of the abutment.

11. The implant of claim 9, wherein the base portion of the tabs is adjacent the abutment such that the abutment extends further from the axis in a radial direction than the base portion of the tabs.

12. The implant of claim 7, wherein both the median and connecting zones are substantially planar.

13. The implant of claim 7, further comprising a second fixation zone extending along the axis away from the connecting zone, the second fixation zone formed of shape-memory material such that the second fixation zone is capable of changing shape by shape-memory action at body temperature.

14. The implant of claim 13, wherein the second fixation zone includes a length and a slot along a portion of the length, wherein the slot of the second fixation zone has a narrow oblong shape prior to changing shape by shape-memory action at body temperature and a wide oblong shape, which is wider than the narrow oblong shape, after changing shape by shape-memory action at body temperature.

15. An implant suitable for implantation in bone, comprising:
a median zone extending along a longitudinal axis between a first end and a second end, the median zone is of generally triangular shape tapering from the first end towards the second end;
a first fixation zone extending from the first end of the median zone, the first fixation zone formed of shape-memory material such that the first fixation zone is capable of changing shape by shape-memory action at body temperature;
a connecting zone extending from the second end of the median zone; and
a second fixation zone extending from the connecting zone, the second fixation zone formed of shape-memory material such that the second fixation zone is capable of changing shape by shape-memory action at body temperature,
wherein the median zone, connecting zone and first and second fixation zones are each implanted within at least one of a first bone portion, a second bone portion, or a space between the first and second bone portions.

16. The implant of claim 15, wherein the first fixation zone includes a pair of tabs formed of the shape-memory material extending from a base portion of the tabs adjacent the first end, wherein the pair of tabs are separable from one another by shape-memory action at body temperature.

17. The implant of claim 15, wherein the second fixation zone includes a second pair of tabs constructed of the shape-memory material and having outer ends that are joined unitarily together such that they form a throughgoing planar slot permitting transverse expansion by shape-memory action at body temperature.

18. The implant of claim 15, wherein the median zone further includes, at the first end, a face extending generally perpendicular to the axis to form an abutment having a width.

19. The implant of claim 18, wherein the width of the abutment is wider than a width of the connecting zone and a width of a base portion of the first fixation zone.

20. The implant of claim 19, wherein the median zone includes a pair of side faces extending from the abutment at the first end and converging towards one another to the second end.

* * * * *

UNITED STATES PATENT AND TRADEMARK OFFICE
CERTIFICATE OF CORRECTION

PATENT NO. : 9,283,007 B2  
APPLICATION NO. : 13/897775  
DATED : March 15, 2016  
INVENTOR(S) : Marc Augoyard et al.

Page 1 of 1

It is certified that error appears in the above-identified patent and that said Letters Patent is hereby corrected as shown below:

On the Title Page, Item (63) Related U.S. Application Data: "Continuation of application No. 11/911,405, filed as application No. PCT/FR2006/050435 on Oct. 19, 2006, now Pat. No. 8,475,456.)" should read --Continuation of application No. 11/911,405, filed as application No. PCT/FR2006/050435 on Apr. 12, 2006, now Pat. No. 8,475,456.--

Signed and Sealed this  
Thirty-first Day of May, 2016

Michelle K. Lee  
*Director of the United States Patent and Trademark Office*